United States Patent
Niichel et al.

(10) Patent No.: US 10,765,635 B2
(45) Date of Patent: Sep. 8, 2020

(54) MULTIPARTICULATE INCLUDING PHARMACEUTICAL OR PROBIOTIC ACTIVE INGREDIENTS FOR DELIVERY VIA A SHELF STABLE LIQUID DOSAGE FORM

(71) Applicant: Nano Pharmaceutical Laboratories LLC, Denver, CO (US)

(72) Inventors: Robert Niichel, Greenwood Village, CO (US); Samuel Reinhold, III, Denver, CO (US); Clayton J. Nelsen, Aurora, CO (US); Dan A. Finkbeiner, Erie, CO (US); Roy J. McDaniel, Denver, CO (US); Andrew D. Padilla, Westminster, CO (US)

(*) Notice: Subject to any disclaimer, the term of this patent is extended or adjusted under 35 U.S.C. 154(b) by 0 days.

(21) Appl. No.: 16/269,130

(22) Filed: Feb. 6, 2019

(65) Prior Publication Data

US 2019/0240163 A1 Aug. 8, 2019

Related U.S. Application Data

(60) Provisional application No. 62/627,107, filed on Feb. 6, 2018.

(51) Int. Cl.
*A61K 9/50* (2006.01)
*A61K 9/00* (2006.01)
(Continued)

(52) U.S. Cl.
CPC .......... *A61K 9/5073* (2013.01); *A61K 9/0095* (2013.01); *A61K 9/5042* (2013.01); *A61K 9/10* (2013.01); *A61K 2035/115* (2013.01)

(58) Field of Classification Search
CPC ...... A61K 9/5073; A61K 9/5042; A61K 9/10; A61K 2035/115
See application file for complete search history.

(56) References Cited

U.S. PATENT DOCUMENTS 9,149,439 B2 10/2015 Patel et al.
2006/0240105 A1 10/2006 Devane et al.
(Continued)

FOREIGN PATENT DOCUMENTS

EP 0377518 B1 2/1996
WO WO 2014152338 * 9/2014

OTHER PUBLICATIONS

Hypromellose Acetate Succinate AQOAT Shin-Etsu 1987.*
(Continued)

*Primary Examiner* — Blessing M Fubara
(74) *Attorney, Agent, or Firm* — Perkins Coie LLP

(57) ABSTRACT

Various embodiments of modified-release multiparticulates (in bead or granule from) are described. The modified-release multiparticulates can comprise a core including a pharmaceutical and/or probiotic agent, optionally with additional excipients or binders to aid in creation of the core, one or more functional coatings disposed on the core and configured to provide a modified-release profile of the pharmaceutical and/or probiotic agent when given orally, and a coating of hypromellose acetate succinate (HPMCAS) disposed on the one or more functional coatings and configured to impart multiparticulate stability in aqueous acidic media. Suspensions including the modified-release multiparticulates are also described.

7 Claims, 7 Drawing Sheets

(51) Int. Cl.
    *A61K 35/00*    (2006.01)
    *A61K 9/10*     (2006.01)

(56) References Cited

U.S. PATENT DOCUMENTS

| | | | | |
|---|---|---|---|---|
| 2007/0292511 A1* | 12/2007 | Kolatkar | ............. | A61K 9/5026 |
| | | | | 424/471 |
| 2011/0136747 A1* | 6/2011 | Paterson | ................ | A61K 38/08 |
| | | | | 514/21.7 |
| 2011/0311626 A1* | 12/2011 | Venkatesh | ............ | A61K 9/0056 |
| | | | | 424/468 |
| 2013/0323362 A1* | 12/2013 | Penhasi | ................. | A21D 8/045 |
| | | | | 426/61 |
| 2014/0221414 A1* | 8/2014 | Kulkarni | ................. | A61K 9/10 |
| | | | | 514/279 |
| 2015/0164831 A1* | 6/2015 | Roberts | ................ | A61K 9/0095 |
| | | | | 424/464 |
| 2019/0160115 A1* | 5/2019 | Falb | ....................... | A61K 35/74 |

OTHER PUBLICATIONS

Tanno, F. et al. "Evaluation of hypromellose acetate succinate (HPMCAS) as a carrier in solid dispersions," Abstract only, Drug Dev. Ind. Pharm. Jan. 2004, 30(1): 9-17.

International Search Report and Written Opinion dated May 23, 2019 by the Russian International Search Authority, Moscow, for PCT/US2019/016869 filed Feb. 6, 2019, Applicant: Niichel, Robert et al., 8 pages.

* cited by examiner

| Lot # | 1st Coating | 2nd Coat | Media Type | % Active Released after 26 Weeks at 21°C | % Active Remaining in Multi-particulate after 26 Weeks at 21°C |
|---|---|---|---|---|---|
| 16-1075 | 20% WG Ethylcellulose/HPMC Aqueous | N/A | Mock | 100.3% ± 5.4% | 0% |
| 16-1075 | 20% WG Ethylcellulose/HPMC Aqueous | N/A | Syrup | 89.9% ± 4.1% | 10.1% |
| CFF3-148 | 70% Hydrogenated Cottonseed Oil/Beeswax (80:20) | N/A | Mock | 67.5% ± 3.9% | 32.5% |
| CFF3-148 | 70% Hydrogenated Cottonseed Oil/Beeswax (80:20) | N/A | Syrup | 64.5% ± 3.1% | 35.5% |
| CFF3-146 | 20% WG Ethylcellulose/HPMC Solvent | N/A | Mock | 98.3% ± 4.0 | 1.70% |
| CFF3-146 | 20% WG Ethylcellulose/HPMC Solvent | N/A | Syrup | 73.9% ± % | 36.1% |

FIGURE 5

| Lot # | 1st Coat | Second Coating | Media (Solution) Type | % Active Released after 26 Weeks at 21°C | % Active Remaining in Multiparticulate after 26 Weeks at 21°C |
|---|---|---|---|---|---|
| CFF3-136 | N/A | 60% HPMCAS / Ethylcellulose (50:50) | Mock | 77.6% ±0.5% | 22.6% |
| CFF3-136 | N/A | 60% HPMCAS / Ethylcellulose (50:50) | Syrup | 10.8% ± 1.9% | 89.2% |
| CFF3-151 | N/A | 60% HPMCAS | Mock | 92.5% ± 2.2% | 7.5% |
| CFF3-151 | N/A | 60% HPMCAS | Syrup | 5.6% ± 0.7% | 94.4% |

FIGURE 6

| Lot # | 1st Coating | Second Coating | Media (Solution) Type | % Active Released after 26 Weeks at 21°C | % Active Remaining in Multi-particulate after 26 Weeks at 21°C |
|---|---|---|---|---|---|
| CFF3-147 | 20% WG Ethylcellulose/HPMC Solvent | 60% HPMCAS / Ethylcellulose (50:50) | Mock | 49.7% ± 2.6% | 50.3% |
| CFF3-147 | 20% WG Ethylcellulose/HPMC Solvent | 60% HPMCAS / Ethylcellulose (50:50) | Syrup | 3.3% ± 0.6% | 96.7% |
| CFF3-149 | 70% Hydrogenated Cottonseed Oil/Beeswax (80:20) | 60% HPMCAS / Ethylcellulose (50:50) | Mock | 14.3% ± 1.4% | 85.7% |
| CFF3-149 | 70% Hydrogenated Cottonseed Oil/Beeswax (80:20) | 60% HPMCAS / Ethylcellulose (50:50) | Syrup | 2.2% ± 0.1 | 97.8% |
| CFF3-145 | 20% WG Ethylcellulose/HPMC Solvent | 60% HPMCAS | Mock | 87.1% ± 3.2% | 12.9% |
| CFF3-145 | 20% WG Ethylcellulose/HPMC Solvent | 60% HPMCAS | Syrup | 5.1 % ± 0.1% | 94.9% |
| CFF3-150 | 70% Hydrogenated Cottonseed Oil/Beeswax (80:20) | 60% HPMCAS | Mock | 26.9% ± 1.9% | 71.1% |
| CFF3-150 | 70% Hydrogenated Cottonseed Oil/Beeswax (80:20) | 60% HPMCAS | Syrup | 3.3% ± 0.6% | 96.7% |

FIGURE 7

MULTIPARTICULATE INCLUDING PHARMACEUTICAL OR PROBIOTIC ACTIVE INGREDIENTS FOR DELIVERY VIA A SHELF STABLE LIQUID DOSAGE FORM

CROSS-REFERENCE TO RELATED APPLICATIONS

This application claims the benefit of priority under 35 U.S.C. § 119(e) to U.S. Provisional Patent Application No. 62/627,107, filed Feb. 6, 2018, the entirety of which is hereby incorporated by reference.

BACKGROUND

To date, oral delivery of pharmaceutical and/or probiotic active ingredients has been achieved chiefly through either oral solid dosage forms or refrigerated liquid dosage forms. For oral solid dosage forms, such as a tablet or capsule, the active ingredient is commonly formulated into a powder mixture or granulation, which is then usually compressed into a tablet or encapsulated into a hard-shell capsule. For refrigerated liquid dosage forms, the active ingredient is typically either suspended or dissolved in a dispersion medium for delivery. While a tablet or capsule is usually preferred for many reasons (e.g., taste, ease of dosing, ease of manufacturing, shelf stability, etc.), a liquid dosage form may be preferred in certain instances (e.g., a patient's ability to swallow or a desire for extremely rapid dissolution).

To maintain desired therapeutic blood levels for pharmaceutical and/or probiotic active ingredients delivered orally, dosages are commonly taken multiple times a day. This dosing may be bis in die (b.i.d., 2 times a day), ter in die (t.i.d., 3 times a day), quater in die (q.i.d., 4 times a day), or even more frequently. The frequency of dosing needed to maintain therapeutic levels depends on many parameters, including the effective therapeutic blood level range needed for the active ingredient to maintain its effectiveness, as well as the rate at which the body clears the drug (e.g., half-life of the drug).

While maintaining target therapeutic blood levels is one reason for multiple doses of a drug throughout the day, there are other reasons that a single large dose is not preferred as a dosing regimen. Some active ingredients are unstable in areas of the gastrointestinal tract and an extended-release profile can bypass much of the enzymes or other conditions instigating degradation. Furthermore, some active ingredients can irritate the gastrointestinal tract in large doses and a sudden large dose of the drug can be harmful to the patient. In such instances, multiple smaller doses given throughout the day can lessen or eliminate harmful side effects.

No matter the reason for necessitating multiple doses throughout a day, patient compliance with a frequent dosing regimen remains a serious issue. For those medications that require exact dosing, patients must remember to take them at the specified intervals. Outside influences on patients' daily routines, such as alterations in work, sleep, and/or eating times can lead to missed doses. This problem is also evident for younger patients, such as school age children, who may require multiple doses of a prescription medication throughout the school day.

For those active ingredients that require a higher frequency of dosing, the sustained delivery of active ingredients from the dosage form can decrease the frequency of dosing and overall number of doses needed. By reducing the frequency and number of doses, patient compliance can be vastly improved. Additionally, sustained or extended release of active ingredients can lessen the amount of drug delivered all at once, which in turn results in less patient side effects for those drugs that can be harmful at sudden, high doses.

Advances in oral solid dosage forms (e.g., matrix-based tablets and multiparticulates encapsulated into capsules), have enabled the sustained-release delivery of active ingredients via a single dose. These modified release tablets and capsules can deliver the active ingredient via a specific release profile, such as a sustained, extended release—a slow release over a period of many hours. By providing an extended release profile, the dosing frequency requirements may drop significantly, such as from several times a day to only once or twice per day. Furthermore, such sustained release profiles can dramatically limit the fluctuation in blood drug concentrations (i.e., between peak and trough).

Active-containing multiparticulates which are subsequently encapsulated into capsules can be generally considered as having one of two basic forms: beads or granules. Multiparticulate beads are built through distinct manufacturing processes to create round, spherical beads. These spherical beads typically have ingredients other than the active ingredient that help form the bead and maintain its shape. Additionally, beads normally go through a manufacturing process designed to round them and minimize their surface area. Granules meanwhile, are commonly generated using processes that produce irregularly shaped particles. Like beads, granules can be formed using additional excipients which help the granule form and maintain its shape. However, granules can also be prepared containing only active ingredients through certain processes (e.g., dry granulation and crystallization).

There are many ways that oral solid dosage forms can be designed to generate a modified release profile. These include diffusion-based delivery mechanisms (e.g., matrix or reservoir systems), dissolution-based delivery mechanisms (e.g., matrix or encapsulation systems), and osmotic pressure controlled delivery mechanisms. For tablets, all modified release systems can be employed—dissolution-based, diffusion-based, and osmotic pressure controlled. However, for the modified-release of multiparticulates, the reservoir and encapsulation systems make up the vast majority of successful products. These reservoir and encapsulation multiparticulates can display a modified-release profile through a dissolution-based or diffusions-based delivery mechanism, or some combination of the two.

A common example of multiparticulates displaying a combination of dissolution-based and diffusion-based release mechanisms to generate a sustained release profile involves a functional coating applied to an active ingredient core. First a core granule or bead that includes the active ingredient is manufactured. The core bead or granule may then be coated with mostly insoluble material, with a small amount of soluble material incorporated into this coating layer to create pores during release. Drug release occurs after the soluble components of the coating dissolves, creating a pore network which allows entry of the dissolution fluid. The drug transverses from the core to the outer dissolution fluid through the network following a diffusion model. The rate of drug release is dependent on many parameters which can be modified to attenuate the rate of release, including the coating type, coating thickness, type and quantity of soluble pore former in the coating, size of the multiparticulate, surface area of the multiparticulate, and amount of active ingredient in the core, among many others.

One example of sustained release granules is described in U.S. Published Patent Application No. 2003/0104071. This published patent application describes extended release potassium chloride granules consisting essentially of potassium chloride crystals coated only with ethylcellulose for the sustained release of potassium. The granules in this dosage form can be delivered via a hard shell capsule, or formulated into a tablet that disintegrates after ingesting. The extended release of potassium chloride from the granules decreases the need for frequent dosing throughout the day. The extended release also reduces the side effects commonly seen after a patient is administered large doses of potassium chloride, such as gastrointestinal disturbance, weakness, and circulatory disturbances.

Virtually all the pharmaceutical and/or probiotic products that deliver active ingredients orally via an extended release mechanism are solid dosage forms, namely capsules or tablets, with very few exceptions. With these modified release capsule and tablets, patients that normally are required to take a tablet or capsule many times a day may instead take an extended release product once or twice daily. Often, these modified-release capsules and tablets have a higher total amount of active ingredient in them compared to an immediate release dose, with much of the dose spread out over a longer period of release.

However, with the extended release products limited to tablets and capsules, a huge patient population remains insufficiently served—namely those patients who have trouble swallowing solid dosage forms. These patients—whether they are young children, geriatric, physically limited, or incapacitated—must commonly opt for liquid dosage forms, and as such are limited to the immediate release profile that they commonly display.

There are very few examples of sustained-release products on the market designed for a liquid suspension delivery. One example of a sustained-release pharmaceutical product in a liquid suspension form is described in U.S. Pat. No. 6,001,392. The composition generally includes a drug/resin complex that may be carried in a liquid composition wherein the drug is an antitussive. The drug/resin complex utilizes ion-exchange resins, wherein the drug is adsorbed to the resin via ionic bonds to keep the drug in the bead. The release of the drug over time is controlled using additional coating layers to retard the drug release rate. The amount of active ingredient per weight of the bead may be low due to limited adsorption of the drug onto the resin bead, as well as high amounts of additional coating of the bead to facilitate slow release. Additionally, the manufacturing cost of the drug/resin complex is very high, leading to very limited adoption of this technology in the pharmaceutical and/or probiotics industry.

SUMMARY

Disclosed herein are various embodiments of modified-release multiparticulates (in bead or granule from) comprising a core including pharmaceutical agent and/or probiotic, optionally with additional excipients or binders to aid in creation of the core, one or more functional coatings disposed on the core and configured to provide a modified-release profile of the pharmaceutical agent when given orally, and a coating of hypromellose acetate succinate (HPMCAS) disposed on the one or more functional coatings and configured to impart multiparticulate stability in aqueous acidic media.

Reference to multiparticulates herein should be interpreted as including both a bead form of the multiparticulate and a granule form of the multiparticulate, unless expressly stated otherwise. Reference to active or active ingredient herein should be interpreted as including a pharmaceutical, a probiotic, or both.

The multiparticulate described herein can display a modified-release profile, wherein the release rate of the active from the core into the surrounding media is slowed through formulation design. Synonyms of modified-release include both "controlled-release" and "timed-release". Example subtypes of modified-release include 1) delayed-release, where the release of the active ingredient is very slow until some later time point, where the release rate of the active is suddenly accelerated, 2) sustained-release, where the active ingredient is designed to be released at a steady rate, and 3) pulsatile-release, where the active ingredient is designed to be released in bursts, with intermittent periods of no/slow release with faster release of the active. The multiparticulates described herein may display any version of a modified-release profile including delayed-release, sustained-release, and pulsatile-release.

In some embodiments described herein, the modified-release multiparticulate may be dispersed in an acidic aqueous liquid media, thereby creating a suspension capable of facilitating delivery of the ingredients to patients or consumers in a drinkable or easily swallowable/ingestible form. The modified-release multiparticulates display stability at room temperature in the acidic aqueous-based media, with primarily all of the active ingredient remaining in the multiparticulate prior to ingestion.

In some embodiments of the liquid stable modified-release multiparticulate described herein, the core contains only active ingredient, with no other binders in the core.

In some embodiments, the only excipients included in the core are excipients that do not swell in water (either water soluble ingredients or water insoluble ingredients), thereby improving the stability of the multiparticulates in the aqueous-based liquid medium. In another embodiment, the multiparticulate contains some excipients that may swell in water, but rupturing of subsequent coating layers during aqueous storage is prevented by increasing the coating strength, thereby giving the multiparticulate additional physical stability during storage.

In some embodiments of the liquid stable modified-release multiparticulate described herein, the one or more functional coatings may be an enteric polymer (e.g., methacrylic acid copolymer), an enteric resin (e.g., shellac), an insoluble cellulose-based polymer (e.g., ethylcellulose), a combination insoluble cellulose-based polymer system with a water-soluble pore former (e.g., ethylcellulose with a water soluble ingredient), a protein-based coating, or a lipid coating.

In some embodiments of the multiparticulates described herein, the one or more functional coatings may not alter the release profile of the multiparticulate or may be omitted altogether, creating a multiparticulate that does not show any substantial sustained-release profile.

In some embodiments of the modified-release multiparticulate described herein, the addition of an outer coating layer comprising hypromellose acetate succinate (HPMCAS) on the multiparticulate gives the multiparticulate stability in acidic (less than pH 7.5) aqueous media. This HPMCAS ingredient includes hyroxypropyl methylcellulose (HPMC) that has been further modified with a mixture of monosuccinic acid and acetic acid esters. In some embodiments, the resulting HPMCAS has between 2% to 16% of actetyl groups (by weight %) and 4% to 28% of succinyl groups (by weight %), which demonstrates acceptable stability in acidic liquid media.

The multiparticulate described herein displays acceptable stability in an acidic aqueous media. This aqueous media may be part of the original commercial dosage form (e.g., a finished bottle containing both multiparticulates and acidic aqueous media), or the acidic aqueous media may be added later to a population of multiparticulates by an appropriate health professional such as a pharmacist, or the acidic aqueous media may be added later to a population of multiparticulates by the end consumer (point of use).

Methods of making the modified-release multiparticulates described herein are also disclosed.

BRIEF DESCRIPTION OF THE DRAWINGS

FIG. 5 is a table containing stability information of different formulations with multiparticulates containing active ingredients prepared and coated with a modified-release coating layer only.

FIG. 6 is a table containing stability information of different formulations with multiparticulates containing active ingredients prepared and coated with a protective coating of HPMCAS coating only.

FIG. 7 is a table containing stability information of different formulations with multiparticulates containing active ingredients prepared and coated with a dual layer of both a modified-release coating layer plus an additional protective coating layer of HPMCAS coating.

DETAILED DESCRIPTION

Figure 1:
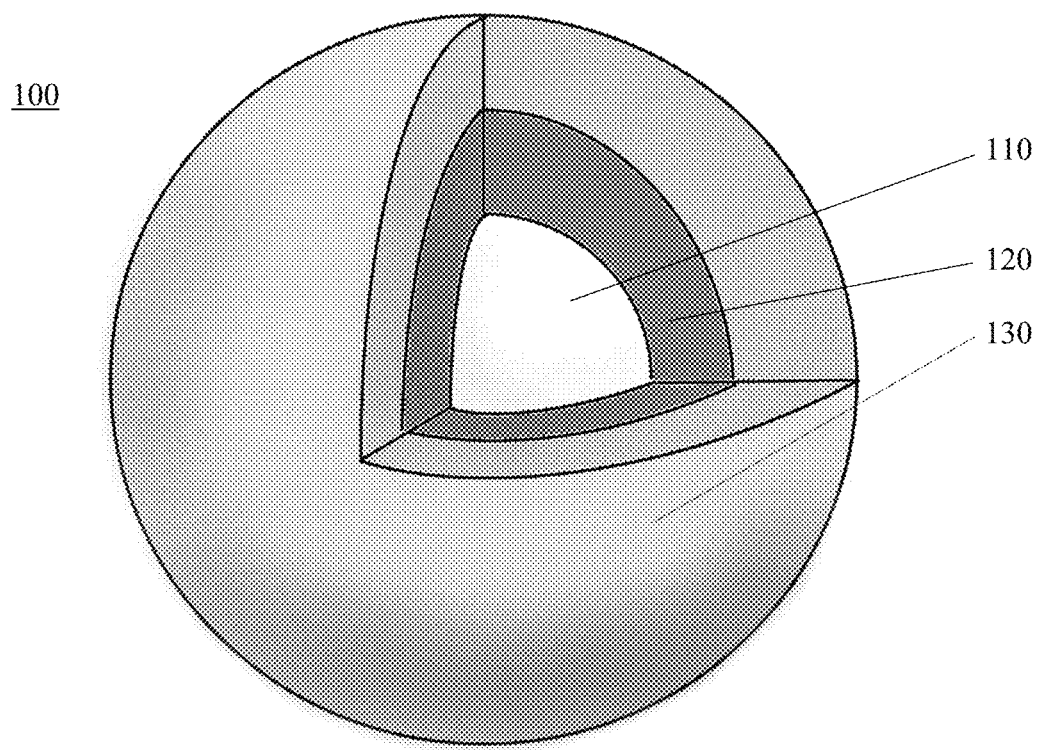
FIG. 1 depicts a modified-release multiparticulate configured in accordance with various embodiments described herein.
Figure 2:
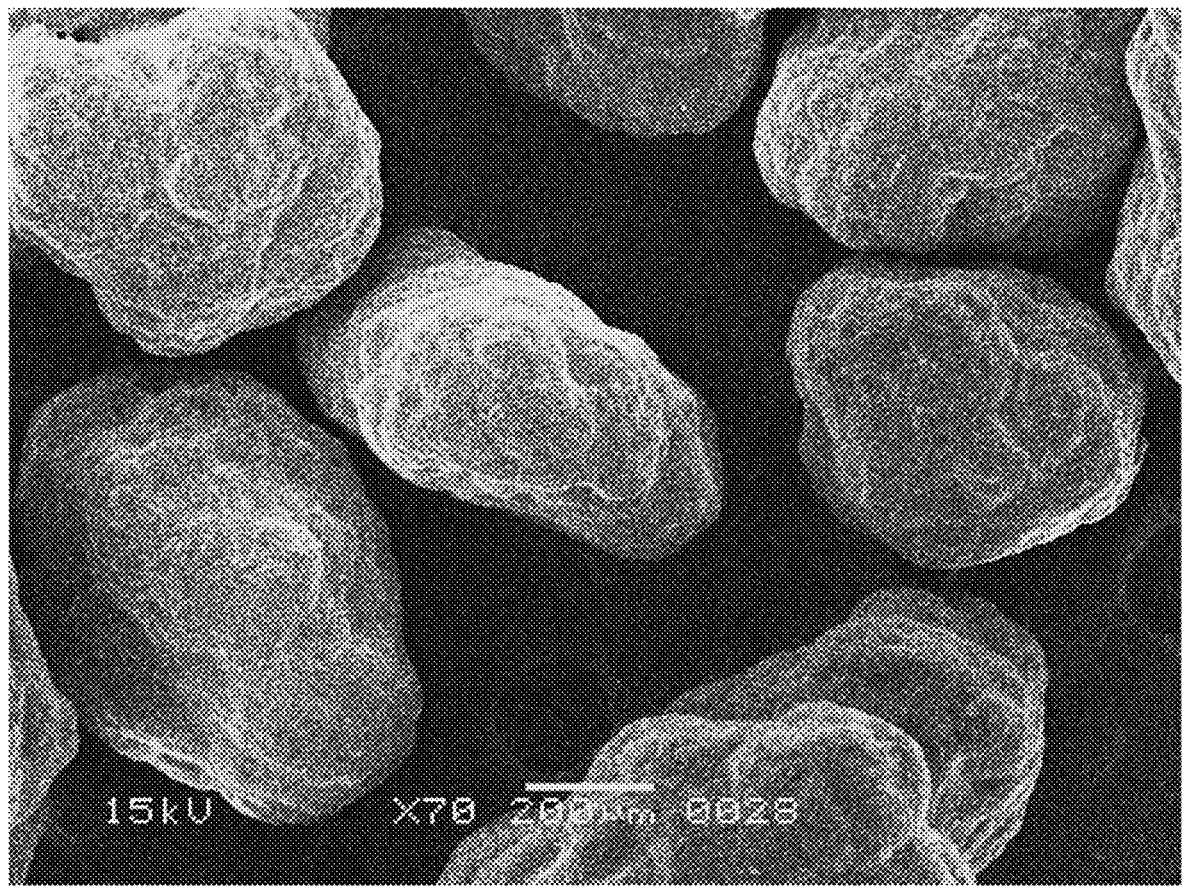
FIG. 2 is an SEM image of modified-release multiparticulate configured in accordance with various embodiments described herein

Described herein are various embodiments of a modified-release multiparticulate generally comprising a core including a pharmaceutical and/or probiotic active ingredient and an outer coating of hypromellose acetate succinate that gives the modified-release multiparticulate substantial stability in acidic aqueous media. The core can be coated with additional rate modifying ingredients to obtain a modified-release multiparticulate. The modified-release multiparticulate, with or without intermediate coatings of rate-modifying ingredients, can be coated with HPMCAS to create a modified-release multiparticulate that displays substantial stability in acidic aqueous media. FIG. 1 illustrates an exemplary multiparticulate configuration wherein both an intermediate coating and an HPMCAS coating are provided. More specifically, FIG. 1 illustrates a multiparticulate 100 in including a core 110, an intermediate coating 120 (e.g., of rate-modifying ingredients) formed around and encapsulating the core 110, and a HPMCAS layer 130 formed around and encapsulating the core 110 and the intermediate coating 120. FIG. 2 provides an SEM image of multiparticulate having the configuration illustrated in FIG. 1.

As noted above, the disclosed multiparticulate includes a core. The core may include one or more pharmaceutical and/or one or more probiotics as active ingredients. In some embodiments, the pharmaceutical or probiotic ingredient is any material that has a pharmacological effect on the body and that is regulated by the United States Food and Drug Administration (FDA) as a drug. The term "drug", as defined in the United States Federal Food, Drug, and Cosmetic Act calls a drug (SEC. 201. [21 U.S.C. 321], Section G):

"(A) The term "drug" means articles recognized in the official United States Pharmacopeia, official Homeopathic Pharmacopeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals; and (D) articles intended for use as a component of any articles specified in clause (A), (B), or (C)."

These pharmaceutical or probiotic ingredients may include, but are not limited to, cough suppressants, expectorants, anti-inflammatory drugs, pain reducing drugs, antihistamines, antibiotics, circulatory system drugs, gastrointestinal drugs, antidepressants, antipsychotics, diabetes drugs, genetic disorder drugs, drugs for viral treatments, etc. The term 'drug' as defined by the US Federal Food, Drug, and Cosmetic Act includes those pharmaceuticals that are distributed by a licensed pharmacist (prescription products) as well as those available over-the-counter (OTC).

In some embodiments, the pharmaceutical and/or probiotic active ingredient is any other material that has a pharmacological effect on the body not regulated by the United States Food and Drug Administration as a drug. This includes nutritional supplements such as stimulants, electrolytes, vitamins, minerals, proteins, probiotics, and amino acids. These active ingredients may have Generally Recognized as Safe (GRAS) status. Specific examples include calcium, magnesium, caffeine, probiotics, theacrine, branch chain amino acids (BCAAs), Vitamin B1, Vitamin B2, Vitamin B3, Vitamin B5, Vitamin B6, and Vitamin B12.

In some embodiments, the pharmaceutical and/or probiotic active ingredient are strains of probiotics. Specific examples include live probiotic strains (e.g., *lactobicillus acidophilus, LactoBacillus brevis, LactoBacillus bulgaricus, LactoBacillus casei, LactoBacillus gasseri, LactoBacillus lactis, LactoBacillus plantarum, LactoBacillus paracasei, LactoBacillus rhamnosus, LactoBacillus salivarius, Bifidobacterium breve, Bifidobacterium Bifidobacterium infantis, Bifidobacterium bifidum, Bifidobacterium lactis, Bifidobacterium longum, Streptococcus thermophiles, Pediococcus acidilactici*, etc.), and spore forming probiotics (e.g., *Bacillus laterosporus, Bacillus coagulans, Bacillus subtilis, Bacillus cereus*, etc.)

In one embodiment, the core contains either all of the pharmaceutical and/or probiotic ingredient present in the multiparticulate, or a lesser subportion of the pharmaceutical and/or probiotic ingredient present in the multiparticulate. The core is not limited in size, and can have a broad range of sizes. One suitable size is 5 microns up to 5 millimeters in size. Alternatively, the cores can be much smaller in size, such as on a nanometer scale. A population of cores may have one uniform size, or may contain a broad distribution in sizes, thereby providing some smaller multiparticulates and some larger multiparticulates within a population of multiparticulates. The core is not limited in shape, and may include spherical cores, cubical cores, rod-like cores, irregularly-shaped cores, flat disc-like cores, or any other shape.

As discussed in greater detail below, the core may contain other components in addition to the one or more pharmaceutical and/or one or more probiotic active ingredients. These additional components include, but are not limited to, solvents, binding agents, carriers, smaller sub-cores, etc. The core may include only pharmaceutical and/or probiotic active ingredient or a combination of pharmaceutical and/or probiotic active ingredient and one or more additional components.

This core itself can be prepared by a plethora of different methods before any additional layers, such as a modified-release layer or a HPMCAS layer, is applied to it.

One possible method of preparation of the core includes wet granulation, where the active ingredient is mixed with a solvent (e.g., water, alcohol, organic solvent, etc.), optionally with one or more binding agents to help facilitate core formation. Wet granulation techniques are various, and include both high shear and low shear processes, as well as fluidized bed granulation and rotary granulation. The wet mass can be dried and milled for further coating or processing. Alternatively, the wet mass can be further processed while still wet, such as being extruded to form more consistently sized and shaped particles. Extruder types include screw extruders, screen extruders, gear extruders, cylinder extruders, and radial extruders. After extrusion, the material can be dried and milled for further coating or processing. Alternatively, after extruding the material can be spheronized using a spheronizer to round the cores, and then subsequently dried for further coating or processing.

Another possible method of preparation of the core includes dry granulation, which includes both roller compaction and slugging. In dry granulation, the active ingredient is forcefully compacted to create material bonded through force. This material is then milled if necessary, and further sieved to an appropriate size. Additional binding ingredients, such as cellulosic polymers, lipids, waxes, or other inert materials, can be included in during compression of the material to aide in the formation of larger cores. In roller compaction, the powder active ingredient material is squeezed between two rollers to produce a sheet of material that is then milled and sized. In slugging, tablets are usually formed using a tablet press, which are then subsequently milled and sized to form cores.

Another possible method of preparation of cores includes melt techniques such as melt extrusion, melt granulation, and spray chilling. In melt extrusion, a carrier such as a polymer or lipid is added to an active ingredient, and the mixture is then added to a machine with screws. The carrier is melted during the process, either from mechanical energy of the mixing or from additional heat applied to the system. By melting the carrier, the active ingredient is mixed with the molten portion, and upon extrusion of the mixture the material solidifies. This solid material can then be further processed to create a core that includes the active ingredient and the carrier. Melt granulation is a process similar to wet granulation, but instead of a liquid added to the granulation, a carrier is selected that will melt during the granulation process. The inert carrier is mixed with the active ingredient, and granulating process melts the carrier. After agglomerating and subsequent cooling, the cores created contain both carrier and active ingredient. Spray chilling, commonly referred to as prilling, is a melt granulation technique where solid particles or powder of the active ingredient are dissolved or dispersed into a molten carrier, which is then sprayed into droplets in a chamber that is at a temperature cooler than the melting point of the carrier. At the cooler temperatures, the droplets congeal into hard spherical cores that contain both active ingredient and the carrier.

A similar method to spray chilling is spray drying, where the active ingredient is dissolved or dispersed into an inert carrier in solution, rather than a molten carrier as in spray chilling. The active ingredient with carrier solution are sprayed into droplets in a chamber, a process also referred to as atomization. The solvent used to dissolve the carrier is evaporated, creating hard spherical cores of active ingredient and inert carrier.

In another embodiment, cores can be created via more advanced chemically-driven processes, such as electrostatic, extrusion/coacervation, or emulsification techniques. These processes often rely on properties of components at the surface to drive core formation. For instance, coacervation utilizes electrostatically-driven liquid-liquid phase separation. In this process, oppositely charged ions help form a droplet that contains the active ingredient. These droplets can be collected and further processed. In emulsion preparations, the cores have the active ingredient dispersed or dissolved in a liquid, which is then added into another liquid that is insoluble or immiscible with the first liquid. When the two immiscible liquids are mixed, the resulting droplets containing active ingredient can be further processed. In another embodiment, a core can be created using specialized encapsulation equipment such as the Buchi encapsulator. In this process, droplets are created via the encapsulator device, and an electrode and electrostatic charge generator help disperse the droplets with electrostatic repulsion forces. An agitated gelling bath can be used to foster gelification or polymerization of the droplets to allow the cores to harden.

In another embodiment, a core containing active ingredient can be created by drug layering or powder layering the active ingredient onto a smaller inert core. In this preparation method, a smaller inert core without active ingredient is first made or purchased commercially. Examples of commercially-available smaller inert cores include sugar spheres, microcrystalline cellulose spheres, and wax beadlets. The active ingredient is then layered onto the smaller inert core to build a larger core with active ingredient. This layering process can use a solution that contains the active ingredient along with one or more binding agents that help facilitate adherence onto the smaller inert core during spraying. Binding agents in this preparation can also function as release-rate modifying agents, such as ethycellulose or enteric polymers. While it is common to dissolve the active ingredient in the spray solution, the layering process can also be accomplished by spraying a solvent, such as water, alcohol, or organic solvent, onto a mixture of active ingredient and smaller inert core. The solvent sprayed can dissolve or mobilize the active ingredient, facilitating binding to the smaller inert cores.

In another embodiment, other techniques can be used to create a core containing active ingredient. These other techniques include moisture activated dry granulation, steam granulation, reverse wet granulation, thermal adhesion granulation, melt granulation, freeze granulation, foam granulation, and other less widely-used granulation techniques.

In another embodiment of the modified-release multiparticulates, the core that contains the pharmaceutical and/or probiotic active ingredient is coated first with a modified-release layer (also referred to herein as a functional coating), using a substance that gives the resulting multiparticulate a modified-release profile. This functional coating may include enteric polymer (e.g., methacrylic acid copolymer, cellulose acetate phthalate), an enteric resin (e.g., shellac), an insoluble cellulose-based polymer (e.g., ethylcellulose), a combination insoluble cellulose-based polymer system with a water-soluble pore former (e.g., ethylcellulose in conjunction with a water soluble ingredient), a protein-based coating, a lipid coating, or wax coatings. Other functional ingredients that alter the release profile of the active ingredient may also be used.

The modified-release layer may be applied to the core containing the pharmaceutically active ingredient by a variety of different processes. This layer (or layers) can be applied through solution or dispersion coating using a fluidized bed coating system, wherein the cores are dispersed and the coating is applied by spraying a solution or suspension onto them. The coating medium, whether solvent or aqueous, is removed during the process, allowing the coating layer to solidify onto the core. Such fluid-bed coating methods include top-spray coating, bottom spray coating (also known as Würster coating), tangential spray coating, or variations in between. In other embodiments, the modified-release layer is applied to the core through powder layering, typically using fluid bed processes as well. In this method, the coating ingredient is mixed with the core in a fluid bed and heated, and an additional liquid may be sprayed onto the mixture to facilitate coating. In other embodiments, namely for applying molten lipids or waxes, a material is sprayed onto the cores using a hot melt coating apparatus. Somewhat similar to solution or dispersion coating, hot melt coating is typically done in a fluidized bed that can be equipped in a variety of spray orientations or configurations.

In other embodiments, a modified-release layer can be applied using a solid wall coating pan system, where a solution or dispersion containing the functional ingredient, or a molten liquid, is applied to the cores in a continuously moving coating pan, allow the functional coating ingredient to cover the cores.

In another embodiment, a modified-release layer can be applied using any other technique such that the modified-release layer retards the release of active ingredient from the core.

In some embodiments, the amount of functional coating applied to the cores is dependent on the coating type, the release rate desired, the method of application, the size of the cores, and/or the morphology of the cores. For very spherical, larger cores, using an insoluble coating such as ethylcellulose, a coating amount as little as 3% w/w of the final modified-release multiparticulate may be sufficient. For cores with a more irregular morphology that are functionally coated with a wax coating such as cottonseed oil, a coating amount of 50% w/w of the final modified-release multiparticulate may be needed.

In some embodiments described herein, the modified-release layer may not alter the release profile or may be omitted altogether, creating a multiparticulate that does not show any substantial modified-release profile. Without a modified-release layer, the active ingredient in the finished product does not display a sustained-release. However, the finished product still may display a delayed-release because of the outer coating layer including the enteric hypromellose acetate succinate polymer that facilitates release at neutral pH as described in greater detail below.

The modified-release multiparticulates described herein can further include an additional coating of hypromellose acetate succinate coated directly on the core (in the case where no functional coatings are used) or on the one or more functional layers coated on the core. This hypromellose acetate succinate, also called hydroxypropyl methylcellulose acetate succinate (HPMCAS) is a cellulosic polymer that is water soluble at neutral and basic pH, and insoluble in acidic pH. HPMCAS is made of hyroxypropyl methylcellulose (HPMC) that has been further modified with a mixture of monosuccinic acid and acetic acid esters. Commercially, HPMCAS is available in various forms including Aquasolve™ made by Ashland™, AQOAT® made by Shin-Etsu, and AFFINISOL™ HPMCAS made by Dow Pharmaceutical Solutions. HPMCAS has both Acetyl and Succinoyl groups substituted on the available hydroxyl groups, commonly with different amounts of substitution representing different grades of the polymer. These differing amounts of substitutions and chemical differences give the grades different water vapor permeabilities, different glass transition temperatures, different solvent solubilities, different tensile strengths, different pH solubilities, and other distinct attributes.

In some embodiments, the HPMCAS has between 2% to 16% of actetyl groups (by weight %) and 4% to 28% of succinyl groups (by weight %) to be liquid stable and also facilitate release once the media pH is changed to a more neutral pH. In some embodiments, the HPMCAS should have a viscosity between 2.4 and 3.6 centipose (cP) as measured as a 2% solution in NaOH solution. These characteristics help to ensure proper performance of the disclosed multiparticulate, particularly with respect to stability in acidic aqueous media and subsequent release upon a change to a more neutral pH (>6.5).

HPMCAS can be applied to the coated or uncoated cores via different techniques. The coated or uncoated cores can be dispersed using a fluidized bed or coating pan apparatus, and the HPMCAS polymer may then be applied to the cores via spraying an aqueous dispersion, spraying solvent-based coating, or by dry coating. The HPMCAS polymer adheres to the surface of the cores, building layers and layers of HPMCAS polymer onto the surface. The application process may affect the ability of the coating to resist acidic media; for example, an aqueous dispersion coating system or an ammonia-neutralized coating system may provide less acidic resistance compared to a solvent-based coating process.

The amount of HPMCAS coating applied to the coated or uncoated core is dependent on a number of parameters including the grade of HPMCAS used, the amount of stability needed, the method of application, the size of the cores, the morphology of the cores, and/or the type of modified-release coating (if any) applied prior to the HPMCAS coating. In some embodiments, a wax coating applied to the cores before the coating of HPMCAS lessens the amount of HPMCAS needed to achieve acceptable stability. In general, ranges of 4% to 50% of the finished coated product has been shown to obtain a multiparticulate that is reasonably shelf stable in a variety of acidic aqueous media.

In some embodiments, the HPMCAS coating can be replaced in the formulation by a similar polymer, cellulose acetate phthalate. Cellulose acetate phthalate (CAP) is a biodegradable enteric polymer that has been approved for use in pharmaceutical drug products by the United States Food and Drug Administration. Cellulose acetate phthalate, also called cellacefate, has a CAS number of 9004-38-0. CAP is sold by a few different companies and can be purchased commercially as Eastman C-A-P enteric coating material, FMC's Aquacoat®, and G.M. Chemie Pvt. Ltd.'s cellulose acetate phthalate.

The modified-release multiparticulates containing the pharmaceutical agent, optionally additional excipients, one or more modified-release coatings, and a coating of hypromellose acetate succinate (HPMCAS) described herein demonstrate appreciable multiparticulate stability in aqueous acidic media. This aqueous acidic media can include any aqueous solution wherein the pH is less than 7.5. The aqueous medium may be water, fruit juice, fruit-based, milk-based, soy-based, or the like. In some embodiments, the aqueous medium is a common pharmaceutically utilized dispersion medium used by pharmacists to prepare suspensions for patients, such as Humco's Simple Syrup or Humco's Cherry Syrup. In some embodiments, the dispersion medium is water that may or may not have been treated with additional non-toxic thickening agents used to adjust the dispersion medium to any desired viscosity. Suitable thickening agents include, but are not limited to, agar, xanthan gum, guar gum, gelatin, acacia gum, pectin, ester gum, Arabic gum, and gullan gum. In some embodiments, the dispersion medium is water that may or may not have been treated with additional excipients used to adjust the dispersion medium to any desired osmolarity.

The viscosity of the dispersion medium can range from 0-5 cP (mPa·s) such as water, or as much as 100-250 cP, similar to the viscosities of corn syrup or maple syrup. The viscosity of the dispersion medium may affect the stability of the coated multiparticulates, with increasingly viscous solutions expected to display higher degrees of stability of coated multiparticulates.

Additional components may be included in the dispersion medium, such as components to alter the consistency, appearance, taste, smell, shelf-life, osmolarity, or multiparticulate buoyancy of the modified-release multiparticulate/aqueous medium product.

Stability of the finished, coated multiparticulate refers to the multiparticulate maintaining functionality after appreciable (>2 weeks) storage in the acidic aqueous medium, particularly with respect to two major attributes: 1) the modified-release profile, and 2) retention of the active ingredient in the multiparticulate (i.e., assay/content of the active ingredient of the multiparticulates). With respect to this, when the modified-release multiparticulates are applied with enough material, the HPMCAS coating can protect the contents of the modified-release multiparticulates such that more than 90% of the active ingredient is retained within the multiparticulates for periods of two weeks, 1 month, 3 months, 6 months, 12 months, or even longer when stored at ambient (25 degrees Celsius) conditions in an acidic aqueous solution (pH <7.5). The stability of the finished, HPMCAS coated multiparticulates in such an acidic aqueous media is generally thought to follow the Arrhenius equation, a widely-used formula for predicting the temperature dependence of reaction rates. The Arrhenius equation predicts the stability of the modified-release multiparticulates coated with HPMCAS will be greater at lower (e.g., refrigerated conditions) temperatures. In other words, a finished product that displays acceptable stability at ambient conditions 25 degrees Celsius will display improved stability at lower (e.g., refrigerated, 4 degrees Celsius) conditions. As stated previously, this stability the HPMCAS relates to not only the retention of active ingredient into the core, but also maintaining the modified-release profile, such that the release profile of the multiparticulates does not appreciably change after storage.

Stability information of different formulations can be seen in the Tables shown in FIGS. 5-7. Multiparticulates containing active ingredients were prepared and coated with A) a modified-release coating layer only (FIG. 5), B) a protective coating of HPMCAS coating only (FIG. 6), or C) a dual layer of both a modified-release coating layer plus an additional protective coating layer of HPMCAS coating (FIG. 7). Multiparticulates were placed into one of two aqueous environments at room temperature (70° F.) for four weeks. The two acidic aqueous media used for evaluation of coated multiparticulate stability were a) a mock beverage solution, acidified to a pH <4.0, with a small amount of additional gums, sugars, and preservatives added and b) a mock pharmaceutical syrup (such as Humco's Simple Syrup) that is commonly used in the pharmacy industry. As FIG. 5 shows, a modified-release coating layer only shows little to no stability at 4 weeks in both acidic aqueous media. As FIG. 6 shows, a HPMCAS coating layer shows improved stability in both acidic aqueous media at 4 weeks. And as FIG. 7 shows, a dual coating multiparticulate, with a modified-release underlying coating with an additional HPMCAS protective coating on top shows a significantly improved stability profile for multiple formulations.

Once the modified-release multiparticulates are placed into the dispersion medium, the product may be consumed by patients at any time during the shelf life. The aqueous suspension, including the finished coated multiparticulates, may be consumed in entirety in one dose, such as individually unit dosed vials or bottles. Alternatively, the product may be consumed via multiple doses, such that doses of the suspension are measured out by the consumer for each individual dose. These individual doses may be measured out via pouring into a metered cup, extracted through a metered syringe, or through similar means to ensure a consistent and accurate volume of suspension is dosed to the patient.

The suspendability (i.e., buoyancy) of the multiparticulates in the medium can be controlled by the adjusting the density and viscosity of the dispersing medium. Generally, a medium that has similar density to that of the coated multiparticulates will allow longer periods of multiparticulates suspension after agitating the suspension. Alternatively, the suspendability can be modified by adjusting the density, shape, size, and wettability of the modified-release multiparticulates.

The size and shape of the modified-release multiparticulates coated with HPMCAS are not limited. The shape of the coated multiparticulates may be spherical, cubical, cylindrical, rod-like, plate-like, or any type of irregular shape. A suitable range for the multiparticulates is less than 4.5 mm, such as from 0.1 mm to 4.5 mm. The modified-release multiparticulates may also be much smaller, down to a nanometer scale. FIG. 2 shows an image, taken by Scanning Electron Microscopy (SEM), of a multiparticulate that has been coated with both a modified-release layer and then a protective layer of HPMCAS.

Any active ingredients can be included in the core for modified-release. Exemplary active ingredients include, but are not limited to, nutraceuticals, vitamins, supplements, minerals, enzymes, probiotics, bronchodilators, anabolic steroids, analeptics, analgesics, proteins, peptides, antibodies, vaccines, anesthetics, antacids, antihelmintics, anti-arrthymics, antibiotics, anticoagulants, anticolonergics, anticonvulsants, antidepressants, antidiabetics, antidiarrheals, anti-emetics, anti-epileptics, antihistamines, antihormones, antihypertensives, anti-inflammatories, antimuscarinics, antimycotics, antineoplastics, anti-obesity drugs, antiprotozoals, antipsychotics, antispasmotics, anti-thrombics, antithyroid drugs, antitussives, antivirals, anxiolytics, astringents, beta-adrenergic receptor blocking drugs, bile acids, bronchospasmolytic drugs, calcium channel blockers, cardiac glycosides, contraceptives, corticosteriods, diagnostics, digestives, diuretics, dopaminergics, electrolytes, emetics, haemostatic drugs, hormones, hormone replacement therapy drugs, hypnotics, hypoglycemic drugs, immunosuppressants, impotence drugs, laxatives, lipid regulators, muscle relaxants, pain relievers, parasympathicolytics, parasympathicomimetics, prostagladins, psychostimulants, sedatives, sex steroids, spasmolytics, sulfonamides, sympathicolytics, sympathicomimetics, sympathomimetics, thyreomimetics, thyreostatic drugs, vasodialators, and xanthines; drugs or medicaments, breath fresheners, vitamins and other dietary supplements, minerals, caffeine, nicotine, fruit juices, and the like, and mixtures thereof. Examples of useful drugs include ace-inhibitors, antianginal drugs, antiarrhythmias, anti-asthmatics, anti-cholesterolemics, analgesics, anesthetics, anti-convulsants, anti-depressants, anti-diabetic agents, anti-diarrhea preparations, antidotes, antihistamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, which is currently marketed as Viagra®, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids such as bromocryptine or nicotine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

The active ingredients included in the core can be coated with a modified-release coating layer to ultimately make a suspension of modified-release multiparticulates. This ultimately allows the delivery of a modified-release product via a liquid suspension form, thus reducing the need for frequent dosing. The embodiments described herein provide the means for a modified-release finished product in a liquid suspension form.

Once the pH is of the surrounding media is brought to a neutral or basic pH (above pH 5), the HPMCAS containing coating layer can either dissolve or made permeable enough for water to enter the modified-release multiparticulate and subsequently allow the active ingredient to slowly exit the core. The release rate of the active ingredient can be all at once, or can be designed to be a slower sustained release.

Figure 3:
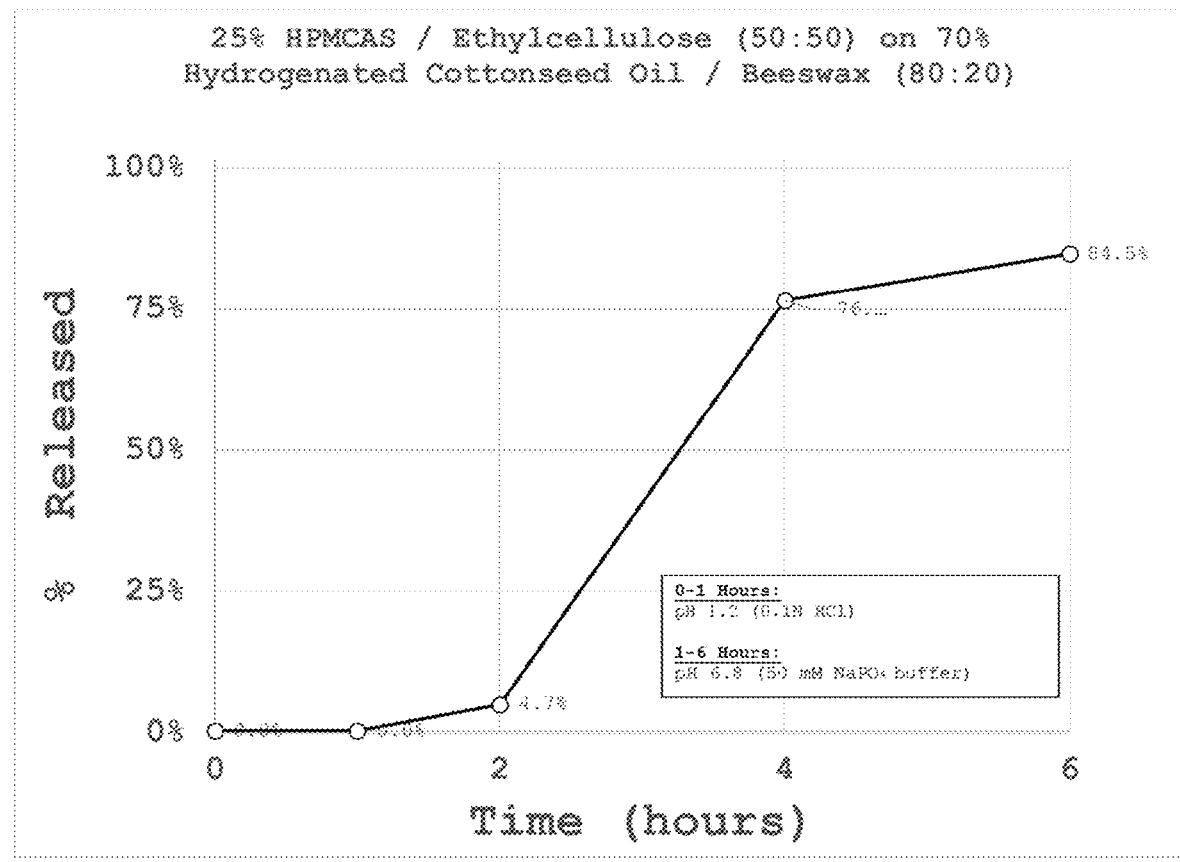
FIG. 3 is a graph of a release curve for modified-release multiparticulate configured in accordance with various embodiments described herein.
Figure 4:
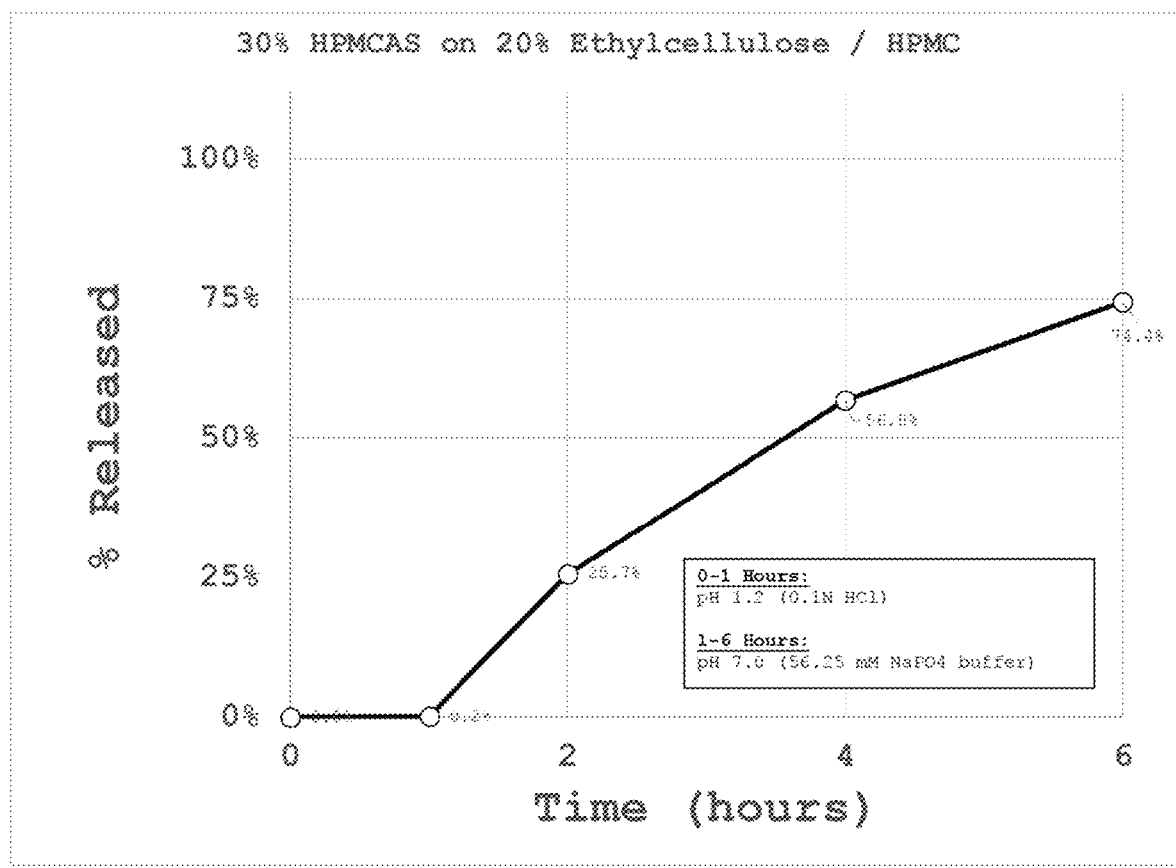
FIG. 4 is a graph of a release curve for modified-release multiparticulate configured in accordance with various embodiments described herein. an example of a release curve wherein 70% of the active ingredient is released in 6 hours in a formulation where the modified-release layer contains a lipid coating of ethylcellulose and HPMC.

FIGS. 3 and 4 depict possible release curves wherein 80% of the active ingredient is released in 6 hours. In one embodiment, longer release profiles are targeted, such as a 12 hour sustained release profile. In one embodiment, a release profile of complete active ingredient release in 15 minutes (i.e. immediate release) are targeted.

Alternatively, in some embodiments, the modified-release layer can be reduced or eliminated entirely, creating a core of active ingredient that is coated with HPMCAS before inclusion in an acidic aqueous medium. Without the first layer of a modified-release ingredient, after oral ingestion, the multiparticulate will release its payload immediately upon entrance into the neutral pH that is found in the small intestine. While the multiparticulate may not display a more distinct modified-release profile, because the HPMCAS coating can still prevent diffusion of the active ingredient into the liquid medium, a multiparticulate with improved liquid stability can be created for inclusion into the liquid suspension. This more stable multiparticulate can be particularly useful for active ingredients that are normally susceptible to oxygen or water mediated degradation such as oxidation or hydrolysis. By preventing the active ingredient from being exposed to the liquid acidic medium, a liquid dosage form of the normally unstable active ingredient can be created.

In some embodiments, the active ingredient can be incorporated into the core, the modified-release coating layer, the protective HPMCAS coating layer, or any combinations therein.

EXAMPLES

Example 1

FIG. 3 is a graph of the release curve for a modified-release multiparticulate configured in accordance with embodiments described herein. The multiparticulate specifically includes a modified-release layer containing hydrogenated cottonseed oil and beeswax and an HPMCAS layer. As show in FIG. 3, greater than 80% of the active ingredient is released within 6 hours.

Example 2

FIG. 4 is a graph of the release curve for a modified-release multiparticulate configured in accordance with embodiments described herein. The multiparticulate specifically includes a modified-release layer containing ethylcellulose and HPMC. As show in FIG. 4, greater than 70% of the active ingredient is released within 6 hours.

From the foregoing, it will be appreciated that specific embodiments of the invention have been described herein for purposes of illustration, but that various modification may be made without deviating from the scope of the invention. Accordingly, the invention is not limited expect as by the appended claims.

We claim:

1. A modified-release multiparticulate, comprising:
a core consisting of one or more active ingredients, wherein at least one of the one or more active ingredients is a probiotic;
at least one functional layer encapsulating the core; and
an exterior coating layer encapsulating the core and the at least one functional layer, the exterior coating comprising hypromellose acetate succinate.

2. The modified-release multiparticulate of claim 1, wherein the at least one functional layer comprises an enteric polymer, an enteric resin, an insoluble cellulose-based polymer, a combination insoluble cellulose-based polymer system with a water-soluble pore former, a protein-based coating, a lipid coating, or combinations thereof.

3. The modified-release multiparticulate of claim 1, wherein the at least one functional layer is constituted so as to not alter the release profile of the modified-release multiparticulate.

4. The modified-release multiparticulate of claim 1, wherein the exterior coating consists of hypromellose acetate succinate.

5. The modified-release multiparticulate of claim 1, wherein the hypromellose acetate succinate comprises hyroxypropyl methylcellulose that has been further modified with a mixture of monosuccinic acid and acetic acid esters.

6. The modified-release multiparticulate of claim 1, wherein the hypromellose acetate succinate has between 2 wt % to 16 wt % of actetyl groups and 4 wt % to 28 wt % of succinyl groups.

7. A suspension comprising:
   an acidic aqueous liquid media; and
   a plurality of the modified release multiplarticulate of claim 1 suspended in the acidic aqueous liquid media.

* * * * *